United States Patent
Hamilton (10) Patent No.: US 7,026,593 B2
(45) Date of Patent: *Apr. 11, 2006

(54) EYE-PROTECTION DEVICE HAVING DUAL HIGH VOLTAGE SWITCHING

(75) Inventor: Thomas J. Hamilton, Holland, MI (US)

(73) Assignee: Jackson Products, Inc., St. Charles, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/915,929

(22) Filed: Aug. 11, 2004

(65) Prior Publication Data

US 2005/0057544 A1 Mar. 17, 2005

Related U.S. Application Data

(60) Provisional application No. 60/494,280, filed on Aug. 11, 2003.

(51) Int. Cl.
*G01J 1/20* (2006.01)

(52) U.S. Cl. ............................. 250/201.1; 250/214 B; 349/14

(58) Field of Classification Search ............. 250/201.1, 250/214 B; 345/221; 359/601, 229; 349/14, 349/33

See application file for complete search history.

(56) References Cited

U.S. PATENT DOCUMENTS

| | | | |
|---|---|---|---|
| 2,423,320 A | 7/1947 | Hurley | |
| 2,548,230 A | 4/1951 | Molyneux | |
| 2,761,046 A | 8/1956 | Herrick et al. | |
| 3,137,784 A | 6/1964 | Kasemann | |
| 3,159,844 A | 12/1964 | Haboush | |
| 3,245,315 A | 4/1966 | Marks et al. | |
| 3,575,491 A | 4/1971 | Heilmeier | |
| 3,731,986 A | 5/1973 | Fergason | |
| 3,873,804 A | 3/1975 | Gordon | |
| 3,881,808 A | 5/1975 | Gurtier et al. | |
| 3,881,809 A | 5/1975 | Fergason et al. | |
| 3,890,628 A | 6/1975 | Gurtler | |
| 3,918,796 A | 11/1975 | Fergason | |
| 3,967,881 A | 7/1976 | Moriyama et al. | |
| 4,039,803 A | 8/1977 | Harsch | |
| 4,071,912 A | 2/1978 | Budmiger | |
| RE29,684 E | 6/1978 | Gordon | |
| 4,155,122 A | 5/1979 | Budmiger | |

(Continued)

FOREIGN PATENT DOCUMENTS

DE 2315308 10/1973

(Continued)

*Primary Examiner*—Thanh X. Luu
(74) *Attorney, Agent, or Firm*—Dunlap, Codding & Rogers, P.C.

(57) ABSTRACT

An auto darkening eye protection device comprising a shutter assembly and a control circuit. The shutter assembly is adjustable between a light state and a dark state. The control circuit comprises a sensing circuit, a weld detect circuit, a positive voltage generator, and a negative voltage generator. The sensing circuit senses incident light and provides an output indicative of the incident light. The weld detect circuit receives the output of the sensing circuit, and enables a dark state drive signal to be delivered to the shutter assembly. The positive and negative voltage generators output the dark state drive signal to the shutter assembly to switch the shutter assembly from the light state to the dark state upon enablement by the weld detect circuit. The dark state drive signal includes a high voltage pulse followed by a stable AC waveform. The high voltage pulse is formed by a positive voltage signal and a negative voltage signal.

35 Claims, 6 Drawing Sheets

U.S. PATENT DOCUMENTS

| | | |
|---|---|---|
| 4,237,557 A | 12/1980 | Gordon |
| 4,240,709 A | 12/1980 | Hornell |
| 4,279,474 A | 7/1981 | Belgorod |
| 4,328,490 A | 5/1982 | Usuba et al. |
| 4,385,806 A | 5/1983 | Fergason |
| 4,435,047 A | 3/1984 | Fergason |
| 4,436,376 A | 3/1984 | Fergason |
| 4,540,243 A | 9/1985 | Fergason |
| 4,556,289 A | 12/1985 | Fergason |
| 4,560,239 A | 12/1985 | Katz |
| 4,582,396 A | 4/1986 | Bos et al. |
| 4,664,479 A | 5/1987 | Hiroshi |
| RE32,521 E | 10/1987 | Fergason |
| 4,710,694 A | 12/1987 | Sutphin et al. |
| 4,728,173 A | 3/1988 | Toth |
| 4,759,608 A | 7/1988 | Yang |
| 4,813,766 A | 3/1989 | Keene et al. |
| 4,821,292 A | 4/1989 | Childress |
| 4,863,244 A | 9/1989 | Fuerthbauer et al. |
| 4,877,310 A | 10/1989 | Seachman et al. |
| 4,901,074 A | 2/1990 | Sinn et al. |
| 4,928,181 A | 5/1990 | Harward |
| 5,015,086 A | 5/1991 | Okaue et al. |
| 5,074,647 A | 12/1991 | Fergason et al. |
| 5,113,270 A | 5/1992 | Fergason |
| 5,184,156 A | 2/1993 | Black et al. |
| 5,208,688 A | 5/1993 | Fergason et al. |
| 5,248,880 A | 9/1993 | Fergason |
| 5,252,817 A | 10/1993 | Fergason et al. |
| 5,347,383 A | 9/1994 | Fergason |
| 5,377,032 A | 12/1994 | Fergason et al. |
| 5,420,502 A | 5/1995 | Schweitzer, Jr. |
| 5,519,522 A | 5/1996 | Fergason |
| 5,671,035 A | 9/1997 | Barnes |
| 5,751,258 A | 5/1998 | Fergason et al. |
| 5,880,793 A * | 3/1999 | Gunz et al. .................. 349/14 |
| 6,067,129 A | 5/2000 | Fergason |
| 6,070,264 A | 6/2000 | Hamilton et al. |
| 6,614,409 B1 | 9/2003 | Bae |
| 6,841,772 B1 * | 1/2005 | Hamilton ................ 250/214 B |

FOREIGN PATENT DOCUMENTS

| | | |
|---|---|---|
| EP | 0157744 | 9/1985 |
| EP | 0335056 | 4/1989 |
| EP | 0349665 | 10/1990 |
| FR | 2530-039 A | 1/1984 |
| GB | 325586 | 2/1930 |
| JP | 59-92276 | 7/1980 |
| JP | 59-111102 | 6/1984 |
| SE | 73127334 | 7/1977 |
| SE | 7608690-9 | 2/1979 |
| WO | WO 90/14809 | 12/1990 |

\* cited by examiner

EYE-PROTECTION DEVICE HAVING DUAL HIGH VOLTAGE SWITCHING

CROSS-REFERENCE TO RELATED APPLICATIONS

The present application claims priority to the provisional patent application identified by the U.S. Ser. No. 60/494,280, which was filed on Aug. 11, 2003, the entire content of which is hereby expressly incorporated herein by reference.

DETAILED DESCRIPTION OF THE INVENTION

Figure 1:
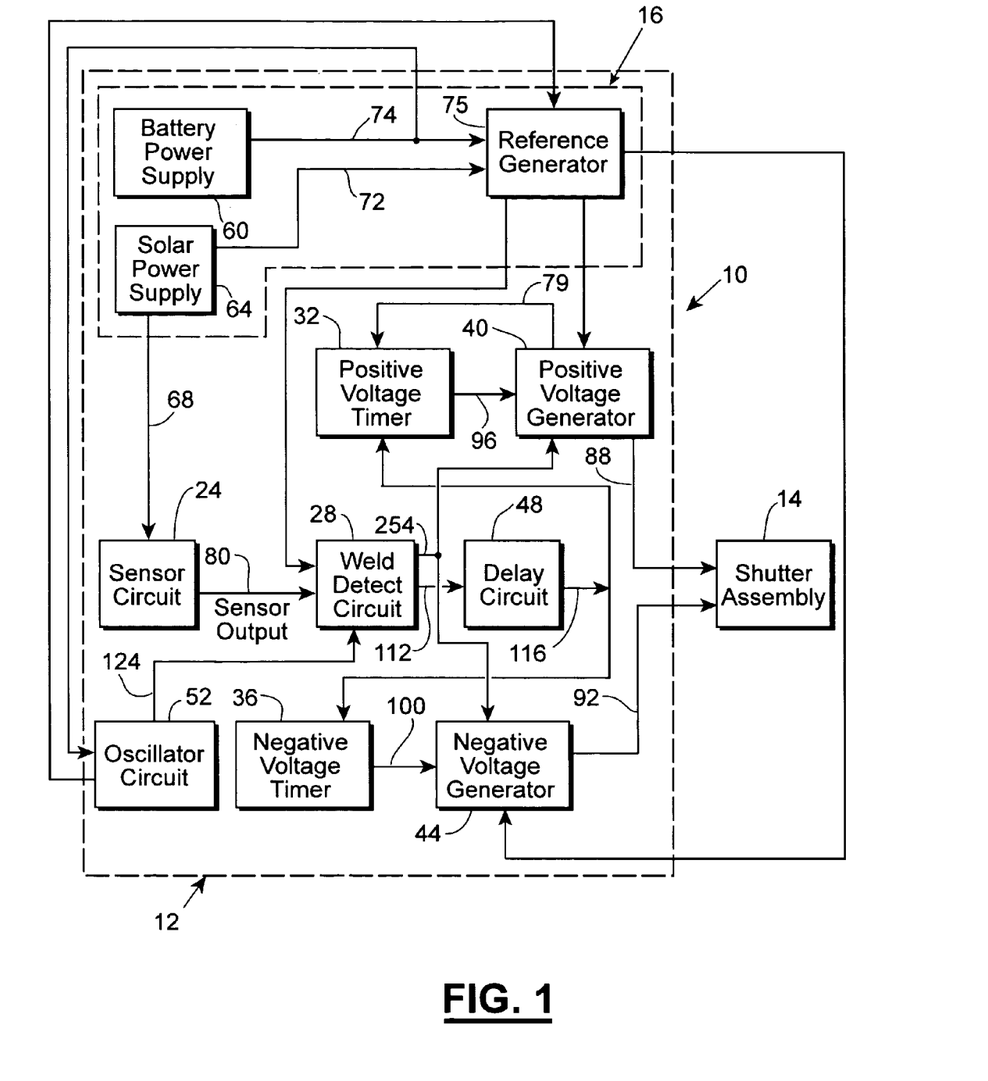
FIG. 1 is a block diagram of an eye protection device constructed in accordance with the present invention.

Referring now to the drawings, and in particular to FIG. 1, shown therein and designated by the reference numeral 10 is an eye protection device constructed in accordance with the present invention. In general, the eye protection device 10 is designed to automatically darken in the presence of an intense light, such as a welding arc. The eye protection device 10 is preferably adapted to be worn by an individual. For example, the eye protection device 10 can be implemented in the form of a cassette 11 (FIGS. 5–9) suitable for mounting in a welding helmet (not shown).

The eye protection device 10 is provided with a control circuit 12, and a shutter assembly 14. The shutter assembly 14 is an auto-darkening filter capable of being driven between a clear state and a dark state. In the clear state, an individual can see through the shutter assembly 14 under ambient light conditions. In the dark state, the shutter assembly 14 becomes opaque so that the individual can comfortably see through the shutter assembly 14 in the presence of an intense light, such as a welding arc.

The switching speed of the eye protection device 10 is an important performance attribute of the eye protection device 10. As will be well understood by those skilled in the art, the switching speed is the time period for switching the shutter assembly 14 from the clear state to the dark state. As will be discussed in more detail below, in accordance with the present invention, a dark state drive signal having a high voltage, e.g. 30 V, is provided to the shutter assembly 14 to enhance the switching speed of the shutter assembly 14. The shutter assembly 14 is preferably a liquid crystal display, such as a twisted nematic liquid crystal display.

The control circuit 12 senses the intense light and outputs the dark state drive signal to the shutter assembly 14 to cause the shutter assembly 14 to switch from the light state to the dark state. If the control circuit 12 senses that no welding arc is present, the control circuit 12 will cause a "light state" drive signal to be delivered to the shutter assembly 14.

In general, the control circuit 12 is provided with a power supply 16, a sensor circuit 24, a weld detect circuit 28, a positive voltage timer 32, a negative voltage timer 36, a positive voltage generator 40, a negative voltage generator 44, a delay circuit 48, and an oscillator circuit 52.

The power supply 16 includes a battery power supply 60, and a solar power supply 64. The solar power supply 64 provides electrical power to the sensor circuit 24 via a power line 68. The battery power supply 60 provides electrical power to control circuit 12 via a power line 74.

The battery power supply 60 can be provided with any suitable voltage so as to supply power to the control circuit 12. For example, the battery power supply 60 can be provided with a voltage in a range from about 2.0 V to about 6.5 V. In one embodiment, such as depicted in FIG. 1, the power supply 16 can further include a reference generator 75, wherein the battery power supply 60 provides electrical power to the reference generator 75 so that the reference generator 75 can provide at least one positive reference voltage and at least one negative reference voltage for the control circuit 12. The reference voltages generated by the reference generator 75 are also generally higher in magnitude than the voltage of the battery power supply 60. Since the reference generator 75 provides higher magnitude positive and negative reference voltages, the battery power supply 60 can be provided with a single lower voltage, thus reducing the cost of the battery power supply 60. In one preferred embodiment, the battery power supply 60 has about +3 Volts, and the reference generator 75 generates reference voltages of about +6 Volts and –6 Volts. Although the control circuit 12 is shown in FIG. 2 as being provided with the reference generator 75, one of ordinary skill in the art would recognize that the battery power supply 60 can be provided with voltages so as to provide positive and negative reference voltages for the control circuit 12, thus eliminating the need for the reference generator 75.

Figure 2A:
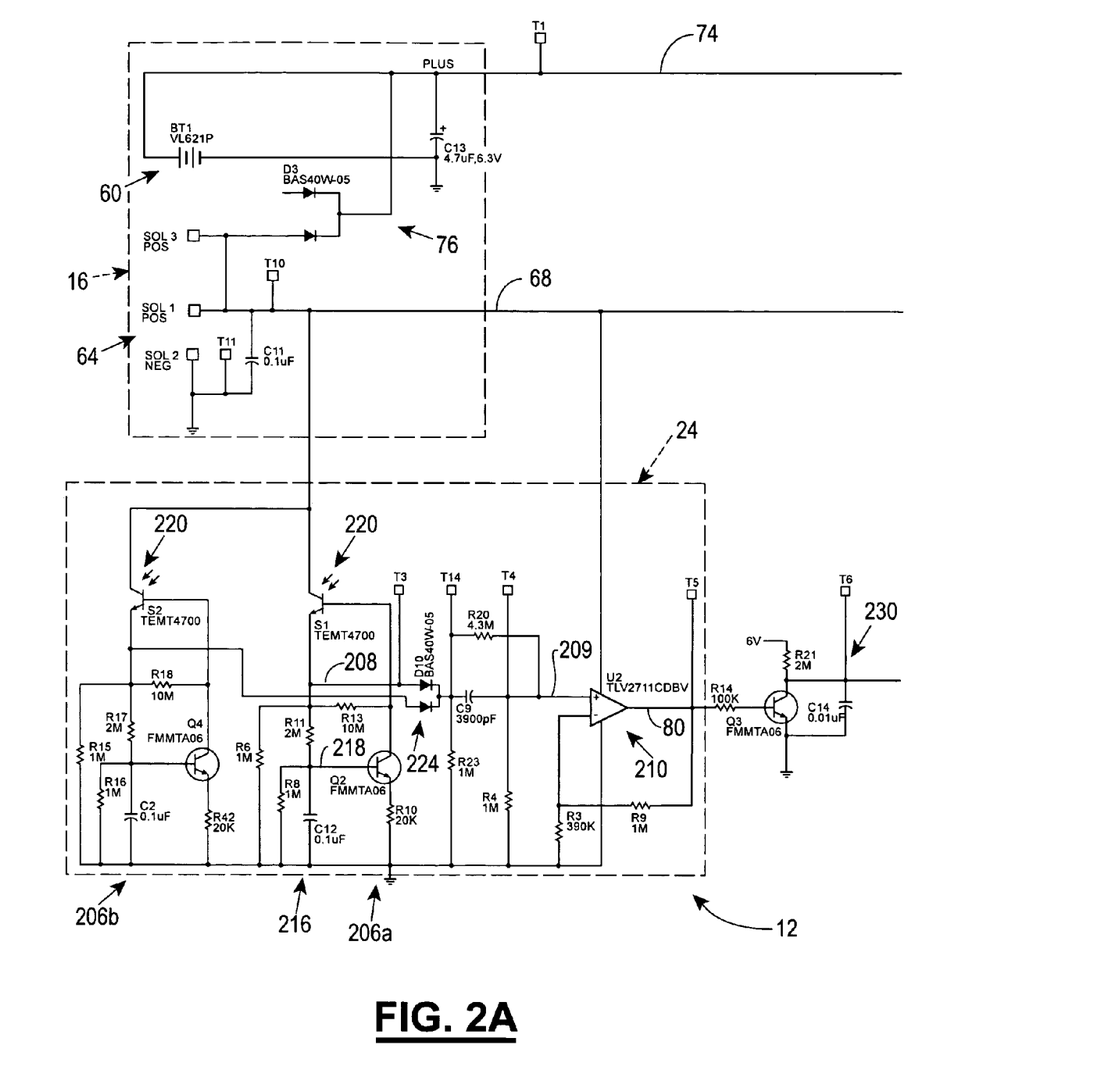
FIG. 2 is a schematic diagram of one embodiment of a control circuit constructed in accordance with the present invention for controlling a shutter assembly.
Figure 2B:
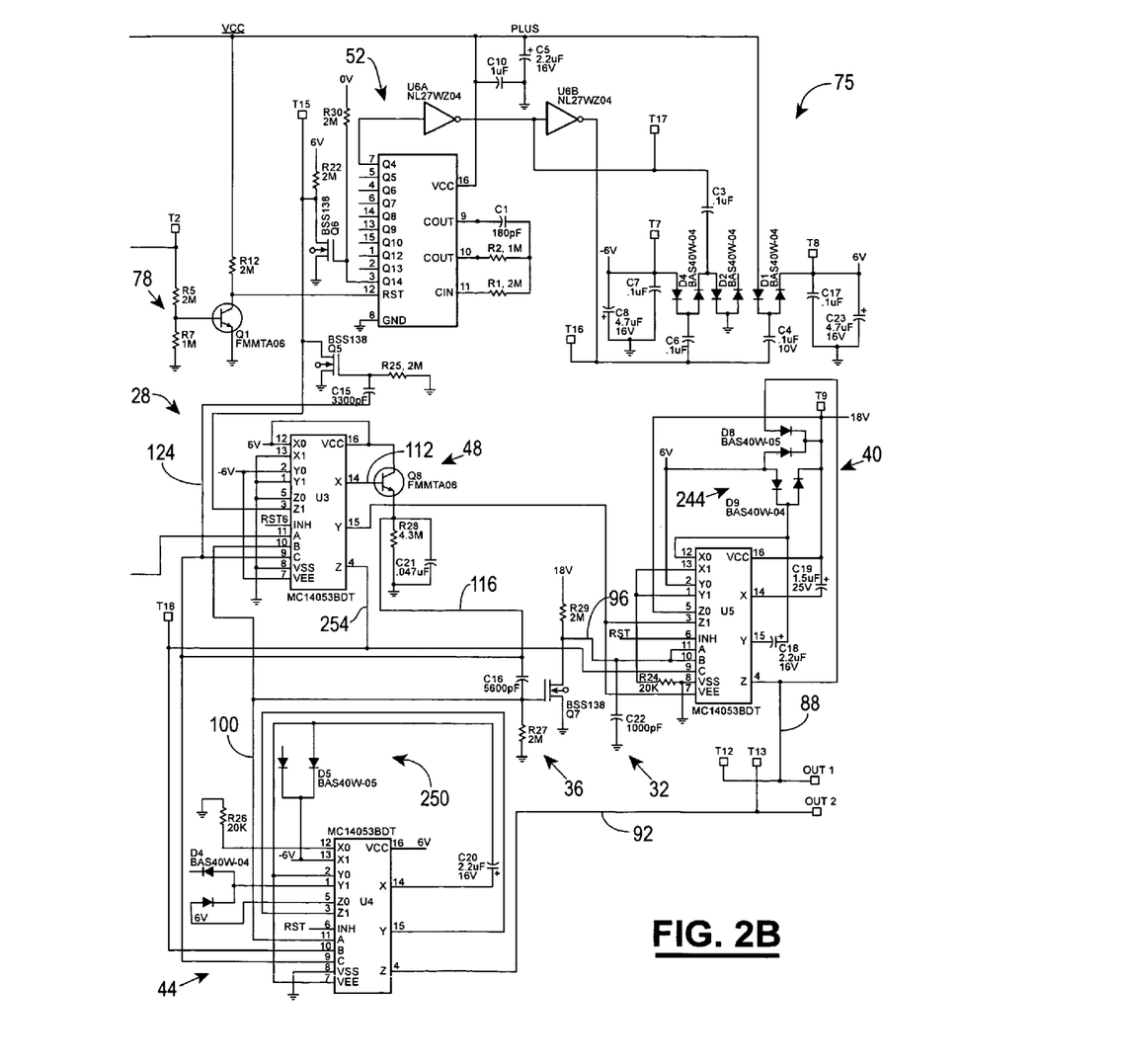

In a preferred embodiment depicted in FIG. 2, the reference generator 75 of the control circuit 12 is a charge pump which converts an essentially square waveform output from the oscillator circuit 52 to the desired DC reference voltages (e.g. +6V and –6V) for other elements of the control circuit 12, such as for example, the weld detect circuit 28, the positive voltage generator 40, and the negative voltage generator 44. Charge pumps are well known by those of ordinary skill in the art, therefore no further discussion of their operation is deemed necessary.

Figure 3:
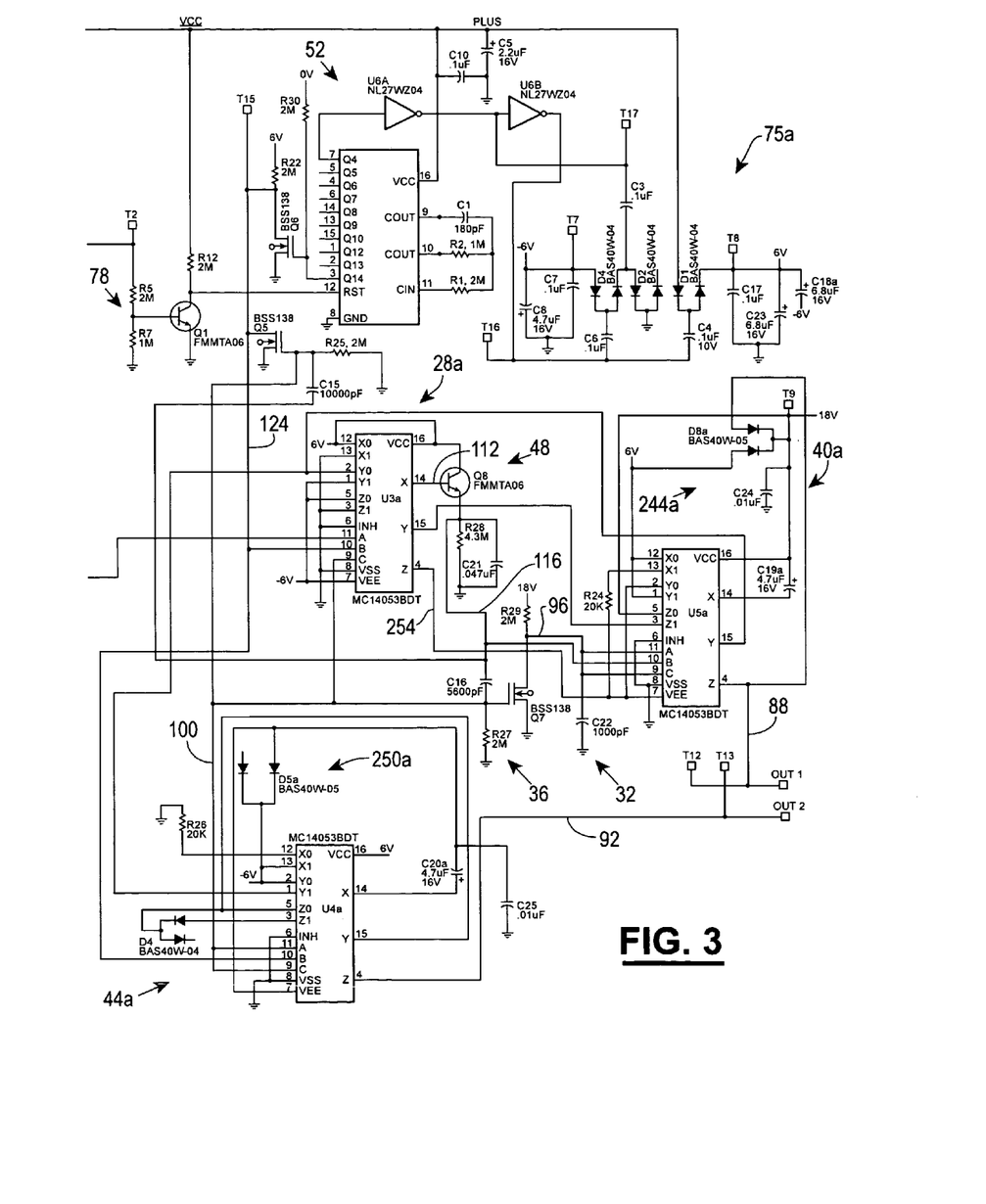
FIG. 3 is a schematic diagram of another embodiment of a control circuit constructed in accordance with the present invention for controlling a shutter assembly.

In one embodiment, as depicted for example in FIG. 2, the reference generator 75 includes capacitors (as designated by the reference numerals C3, C4, C6, C7, C8, C17, and C23), diodes (as designated by the reference numerals D1, D2, and D4), and inverters (as designated by the reference numerals U6A and U6B). Another embodiment of a reference generator is shown in FIG. 3 and is designated therein by reference numeral 75a. The reference generator 75a is similar to the reference generator 75 shown in FIG. 2, except that the reference generator 75a includes another capacitor C18a, and the value of capacitor C23 has been increased, so as to further stabilize the reference voltages provided by the reference generator 75a.

In one preferred embodiment, the power supply 16 is also provided with a charging circuit 76 receiving output from the solar power supply 64 to charge the battery power supply 60 when the solar power supply 64 generates power above the voltage of the battery power supply 60, thereby extending the life of the battery power supply 60. In one embodiment the charging circuit 76 includes at least one diode, as designated by the reference numeral D3.

To further extend the life of the battery power supply 60, in one preferred embodiment, the solar power supply 64 also provides electrical power to a power conservation circuit 78 via line 68, such as shown in FIG. 2, wherein the power conservation circuit 78 is formed by resistors R5, R7, R12, and transistor Q1. When the solar power supply 64 is left unexposed to incident light, i.e., is not providing electrical power, the power conservation circuit conserves the power of the battery power supply 60 by effectively turning off the oscillator circuit 52, and thus the reference voltages for the control circuit 12. For example, when the welding helmet and/or cassette is laid down or put away in storage and not in use, then the output of the solar power supply 64 will be low and the reset of the oscillator circuit 52 will be high, causing the oscillator circuit 52 to only output low signals so as to prevent the oscillator circuit 52 from outputting oscillating signals. Since there is no oscillating signals output by the oscillator circuit 52, no reference voltages will be generated by the reference generator 75, thereby effectively turning off the weld detect circuit 28, positive voltage generator 40, and negative voltage generator 44 of the control circuit 12. As such, the power of the battery power supply 60 is conserved.

The sensor circuit 24 of control circuit 12 detects the presence of light and outputs a sensor output signal representative of the level of light detected. As shown in FIG. 1, the sensor output signal is outputted to the weld detect circuit 28 via a signal path 80. The weld detect circuit 28 enables the drive signal that will be delivered to the shutter assembly 14. In general, if the sensor output signal indicates to the weld detect circuit 28 that an intense light, such as a welding arc is present, the weld detect circuit 28 will cause a dark state drive signal to be delivered to the shutter assembly 14. If the sensor output signal indicates to the weld detect circuit 28 that no welding arc is present, the weld detect circuit 28 will cause a "light state" drive signal to be delivered to the shutter assembly 14.

The dark state drive signal is provided with two components; a high voltage pulse followed by a stable AC waveform. The high voltage pulse quickly drives the shutter assembly 14 from the light state to the dark state. The stable AC waveform maintains the shutter assembly 14 in the dark state. The high voltage pulse preferably has a voltage in a range from about 15 V to about 120 V, and a time period from about 10 microseconds to about 100 milliseconds. In general, the voltage of the high voltage pulse will depend on the maximum voltage ratings of the components utilized to implement the control circuit 12. In one preferred embodiment, the voltage of the high voltage pulse is about 30 V, and the time period of the high voltage pulse is about 10 ms.

Figure 4:
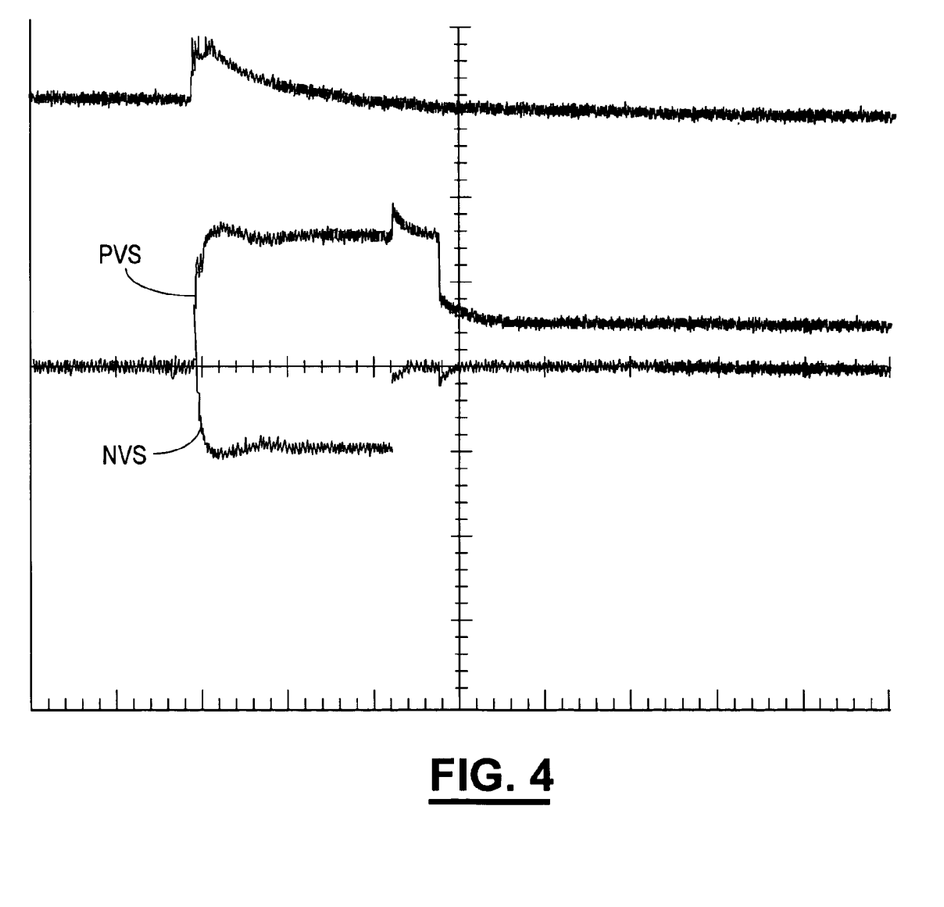
FIG. 4 is a graph illustrating a positive voltage signal and a negative voltage signal in accordance with the present invention.

As shown in FIG. 4, the high voltage pulse is formed by a positive voltage signal (referenced to ground) synchronized with a negative voltage signal (referenced to ground). The positive and negative voltage signals are labeled in FIG. 4 with the designations "PVS" and "NVS". In other words, the leading edges of the positive voltage signal and the negative voltage signals are synchronized. The shutter assembly 14 does not have a ground reference, and therefore, does not differentiate positive or negative. The voltage of the high voltage pulse in the dark state drive signal is thus the difference between the positive voltage signal and the negative voltage signal. For example, if the positive voltage signal has an amplitude of +18 Volts, and the negative voltage signal has an amplitude of −12 Volts, the voltage of the high voltage pulse would be +18 V−(−12 V)=+30 Volts.

The positive voltage signal is produced by the positive voltage timer 32 and the positive voltage generator 40. The negative voltage signal is produced by the negative voltage timer 36 and the negative voltage generator 44. The positive voltage timer 32 sets the time period of the positive voltage signal. The positive voltage generator 40 produces the amplitude of the positive voltage signal. Likewise, the negative voltage timer 36 sets the time period of the negative voltage signal. The negative voltage generator 44 produces the amplitude of the negative voltage signal. In one preferred embodiment, the positive voltage generator 40 triples the voltage of the positive reference voltage provided by the reference generator 75, and the negative voltage generator 44 doubles the negative reference voltage provided by the reference generator 75 so that the high voltage pulse has an effective voltage 5 times the magnitude of the reference voltages of the reference generator 75. Also, in one preferred embodiment, the positive voltage timer 32 receives electrical power (via a signal path 79) having the increased voltage from the positive voltage generator 40 so that the positive voltage timer 32 can switch components in the positive voltage generator 40.

The advantage of using the positive voltage signal and the negative voltage signal is that the cost of manufacturing the control circuit 12 is reduced. That is, electrical components which switch over 18–20 Volts are more expensive than electrical components which switch below 18–20 Volts. By using the positive voltage signal and the negative voltage signal with a magnitude less than or equal to 18–20 Volts (e.g. +18V and −12V), less expensive electrical components can be used to deliver an effective voltage of over 18 Volts (e.g. 30V) to the shutter assembly 14. Further, by providing the positive voltage signal and the negative voltage signal to the shutter assembly 14 directly from the positive voltage generator 40 and the negative voltage generator 44, respectively, use of a costly high voltage driver is not necessary. For example, a high voltage driver is described in more detail in applicant's co-pending patent application identified by the U.S. Ser. No. 10/139,837, the entire contents of which is hereby incorporated by reference.

When the sensor output signal indicates to the weld detect circuit 28 that an intense light, such as a welding arc, is present, the weld detect circuit 28 outputs a signal to the positive voltage timer 32 and the negative voltage timer 36 via delay circuit 48 and signal paths 112 and 116 to cause the positive voltage signal and the negative voltage signal to be fed to the shutter assembly 14 via signal paths 88 and 92. That is, upon receipt of the signal from the weld detect circuit 28, the positive voltage timer 32 and the negative voltage timer 36 output respective timing signals to the positive voltage generator 40 and the negative voltage generator 44 via signal paths 96 and 100. In response thereto, the positive voltage generator 40 outputs the positive voltage signal to the shutter assembly 14 on the signal path 88, and the negative voltage generator 44 outputs the negative voltage signal to the shutter assembly 14 on the signal path 92 to cause the shutter assembly 14 to switch from the light state to the dark state. Then, the weld detect circuit 28 causes the positive voltage generator 40 and negative voltage generator 44 to enable the stable AC waveform to the shutter assembly 14.

The stable AC waveform maintains the shutter assembly 14 in the dark state. The stable AC waveform is preferably an essentially square waveform with a maximum of about +12 Volts to a minimum of about −12 Volts. The stable AC waveform can be provided with other shapes, such as a sinusoidal shape, however, the efficiency of the circuit 12 will be reduced.

In one preferred embodiment, the stable AC waveform is produced as follows. The oscillator circuit 52 provides an oscillating signal to the weld detect circuit 28 via a signal path 124 to cause the weld detect circuit 28 to oscillate the output signals of the positive voltage generator 40 and the negative voltage generator 44 such that the positive voltage generator 40 and the negative voltage generator 44 synchronously output essentially AC waveforms, which are inversely related, to the shutter assembly 14 via lines 88 and 92, respectively. Since the shutter assembly is not referenced to ground, as discussed above, the shutter assembly 14 receives an effective square waveform with a maximum equal to the difference between the maximum of the AC waveform output by the positive voltage generator 40 and the minimum of the AC waveform output by the negative voltage generator 44, and with a minimum equal to the difference between the minimum of the AC waveform output by the positive voltage generator 40 and the maximum of the AC waveform output by the negative voltage generator 44. For example, if the positive voltage generator 40 and the negative voltage generator 44 output essentially inverse synchronous square waveforms with a maximum of +6 Volts and a minimum of −6 Volts to the shutter assembly 14 via lines 88 and 92, respectively, then the stable AC waveform received by the shutter assembly 14 will effectively be a square waveform with a maximum of +12 Volts and a minimum of −12 Volts.

If the sensor output signal indicates to the weld detect circuit 28 that no welding arc is present, the weld detect circuit 28 will cause a "light state" drive signal to be delivered to the shutter assembly 14 via the delay circuit 48, the positive voltage generator 40, the negative voltage generator 44, and the signal paths 112, 116, 92, and 88. The delay circuit 48 delays the submission of the light state drive signal to the positive voltage generator 40 and the negative voltage generator 44 for a predetermined time, thus preventing the shutter assembly 14 from switching to a light state during brief "off" periods in the weld pulsations that exist with various weld types. Further, once the welding arc is extinguished, the work piece which is being welded may glow brightly for several milliseconds thereafter. The delay circuit 48 delays the light state drive signal for desirably between about 0.1 seconds to about 1 seconds, and more desirably between about 0.2 seconds to about 0.4 seconds so as to protect the individual's eyes from the glow from the work piece. The delay circuit 48 may have a fixed time delay, or may be adjustable by a user so as to be set based on the user's preference.

Referring now to FIG. 2, shown therein is a schematic diagram of one preferred implementation of the control circuit 12. The sensor circuit 24 includes one or more phototransistors (only two being shown for purposes of clarity and labeled therein as S1 and S2). The output of each phototransistor S1 and S2 are coupled to a feedback circuit, labeled therein as 206a and 206b respectively. The construction and function of the phototransistors S1 and S2 are similar. Likewise, the feedback circuits 206a and 206b are similar. Thus, only the phototransistor S1 and the feedback circuit 206a will be discussed hereinafter in more detail for purposes of brevity.

Phototransistor S1 serves as the weld sensor. It receives an input of incident light 220 and produces an output on line 208 representative of the intensity of the incident light. The phototransistor S1 used in the present invention is preferably a planar phototransistor configured for a surface mount. The planar phototransistor is smaller than conventional metal can phototransistors, thus allowing a reduction in size of the unit in which the sensor circuit is implemented. While the metal can phototransistors used in the sensor circuits of the prior art had a thickness of about ½ inch, the planar phototransistors with a surface mount used in the present invention have a thickness of only about 1/16–⅛ inch. This reduction in thickness allows the sensor circuit 24 to be implemented into a smaller and sleeker unit. Further, the surface mount configuration of the phototransistor S1 allows the phototransistor to be easily affixed to a circuit board. The inventor herein has found that the TEMT4700 silicon npn phototransistor manufactured Vishay-Telefunken is an excellent phototransistor for the present invention as it has a smaller size than conventional metal can phototransistors and allows the sensor circuit to maintain a constant signal level without excessive loading or the drawing of excessive current.

The feedback circuit 206a for the phototransistor S1 comprises a resistor capacitor circuit 216 connected between the emitter of the phototransistor S1 and ground, and a feedback transistor Q2 having a base coupled to line 218 of the resistor capacitor circuit 216, a collector coupled to the base of the phototransistor S1, and an emitter coupled to the ground via resistor R10. The resistor capacitor circuit 216 and the feedback transistor Q2 in the phototransistor feedback circuit 206a function to adjust the sensitivity of the phototransistor S1. The resistors R11 and R8 and capacitor C12 are chosen to be of a size to provide a relatively large time constant, and therefore a relatively slow response to changes in voltage on line 208. The delay exists because of the time it takes for the voltage on line 218 to charge to an amount sufficiently large to activate transistor Q2. Exemplary values for resistors R11 and R8 are 2 M ohm and 1 M ohm, respectively. An exemplary value for capacitor C12 is 0.1 micro farads. A detailed description of the operation of the resistor capacitor circuit 216 and feedback transistor Q2 can be found in prior U.S. Pat. Nos. 5,248,880 and 5,252,817, the disclosures of which have been incorporated by reference.

The output of phototransistor S1 and feedback circuit 206a is sent to line 208. A load resistor R6 is connected between line 208 and ground. In one embodiment, as shown for example in FIG. 2, line 208 is connected to an OR logical circuit 224, which receives the outputs from the feedback circuits 206a and 206b and permits the highest voltage level from the feedback circuits 206a and 206b to be passed. In one embodiment, the OR logical circuit 224 includes at least two diodes, as designated by the reference numeral D10. Further, the diodes D10 provide isolation between the feedback circuits 206a and 206b.

The output of the OR logical circuit 224 is coupled to line 209 via a capacitor C9. The capacitor C9 forms a filter to block the DC component of the detected signal so that line 209 contains the DC blocked detected signal. The current on line 209 is diverted to ground via resistor R23.

Line 209 is connected to the noninverting input of an amplifier 210. Amplifier 210 is preferably configured as closed loop noninverting amplifier wherein the resistors R3 and R9 form a feedback loop connected to the inverting input of amplifier 210 as shown. Suitable values for R3 and R9 have been found to be 390 K ohm and 1 M ohm, respectively. The output of amplifier 210 on line 80 serves as the sensor circuit output. Line 80 is connected to the input of the weld detect circuit 28 via R14.

The solar power supply 64 of the power supply 16 powers the phototransistor S1 and amplifier 210 via line 68. Thus, if the solar power supply 64 is left unexposed to incident light, phototransistor S1 and amplifier 210 will not receive power, thus preventing the phototransistor S1 and amplifier 210 from draining the battery power supply 60 when the welding helmet is not in use (when not in use, the welding helmet is typically not exposed to intense light). The amplifier 210 may be omitted in other applications or variations of this circuit.

The sensor circuit 24 operates in the presence of both AC welds and DC welds. In an AC weld (also known as a MIG weld), the welding light is pulsating. Thus, the phototransistor S1 will detect a pulsating light signal. The frequency of the pulsations is often 120 Hz. In a DC weld (also known as a TIG weld), the welding light is substantially continuous, with the exception of a small AC component. When an AC weld is present, the phototransistor will produce a pulsating output on line 208. The variations in the voltage signal due to the pulses will be passed through the capacitor C9 to line 209 and fed into the amplifier 210. The amplifier 210 will then provide gain for the signal on line 209 which is sufficient to trigger the delivery of the "dark state" drive signal to the shutter assembly 14.

When a DC weld is present, the phototransistor S1 will quickly produce an output on line 208 catching the rising edge of the DC weld. This sudden rise in voltage on line 208 will be passed through to the amplifier 210 causing a signal on line 80 sufficient to trigger the delivery of a "dark state" drive signal to the shutter assembly 14. Thereafter, capacitor C9 will block the DC component of the DC weld, allowing only the AC variations in the DC weld to pass through to the amplifier 210. A non-reactive element, e.g., resistor R20, is positioned in parallel with a filter circuit formed by capacitor C9, for example. The filter circuit can be a band-pass or a high-pass filter. The non-reactive element provides a DC bias to the input of the amplifier 210 to aid in the detection of the DC weld. That is, the brighter the light being generated from the weld becomes, the more sensitive the sensor circuit 24 becomes. In one embodiment, R20 can have a value of 4.3 M ohm.

The output of the amplifier 210 is fed into the weld detect circuit 28. The weld detect circuit 28 is provided with an electronic switch, an example of which is shown in FIG. 2 as the transistor Q3, a delay circuit 230 and a switching circuit U3.

The delay circuit 230 can be formed of a RC circuit and serves to prevent inadvertent switching of the shutter assembly 14 from the dark state to the light state. That is, the light received by the sensor circuit 24 from the welding arc can be a pulsating signal caused by sputtering of the weld. When the amplifier 210 receives a signal of sufficient magnitude, the output of the amplifier 210 goes high. The high signal is fed to the gate of the transistor Q3. Transistor Q3 then turns on and thereby shorts a capacitor C14 to ground. Once the intensity of the light detected by the sensor circuit 24 decreases, capacitor C14 will begin charging through R21 until the next pulse of intense light is provided to the sensor circuit 24. Thus, the time period of the RC circuit formed by the capacitor C14 and a resistor R21 is selected to maintain the capacitor C14 in a "low" state between pulses to maintain a stable low signal to the switching circuit U3.

The "low" signal is provided to a switch input "A" of the switching circuit U3. This causes the X switch of the switching circuit U3 to switch between the X1 and the X0 inputs. A high signal is applied to the X0 input and the ground reference is applied to the X1 input. Thus, when the low signal is provided to the switch input "A", a high signal is provided to the delay circuit 48 via switch X and the signal path 112.

The delay circuit 48 is provided with an electronic switch as represented by transistor Q8, and an RC circuit as represented by R28 and C21. The high signal switches on the transistor Q8 causing the capacitor C21 to charge. The delay circuit 48 provides a time delay when the control circuit 12 switches from the dark state to the light state. That is, when the welding stops the workpiece may still be glowing brightly. Thus, the time delay of the delay circuit 48 is selected such that the user's eyes will be protected until the glow of the workpiece is diminished. The time delay of the delay circuit 48 can vary widely based on user preference. However, suitable time periods range from about 0.2 seconds to about 0.4 seconds. Suitable values for the resistor R28 and the capacitor C21 are 4.3 M ohm and 0.047 micro farads, respectively.

The positive and negative voltage timers 32 and 36 serve to properly bias the inputs of the positive and negative voltage generators 40 and 44 to generate the high voltage pulse. In one embodiment, the positive voltage timer 32 is formed by resistors R29 and R27, transistor Q7, and capacitors C22 and C16. The negative voltage timer 36 is formed by resistor R27 and capacitor C16. The weld detect circuit 28 triggers both the positive voltage timer 32 and the negative voltage timer 36 such that the positive voltage signal and negative voltage signal are synchronized. In the embodiment depicted in FIG. 2, the positive voltage signal of the high voltage pulse is enabled for a different time duration than the negative voltage signal. However, one of ordinary skill in the art would recognize that the positive voltage timer and the negative voltage timer can be embodied to cause the positive voltage signal and the negative voltage signal to have essentially the same time duration.

In the positive voltage timer 32 and negative voltage timer 36, the emitter of the transistor Q8 is connected to the capacitor C16 via line 116. In the positive voltage timer 32, capacitor C16 is connected to the gate of transistor Q7. Transistor Q7 shorts the capacitor C22, which is connected to switch inputs "A" and "B" of a switching circuit U5 of the positive voltage generator 40. This causes the capacitor C22 to then have to recharge causing the time frame in which the positive voltage generator 40 produces the positive voltage signal of the high voltage pulse. In the negative voltage timer 36, the capacitor C16 is connected to switch input "A" of switching circuit U4 of the negative voltage generator 44 and causes the negative voltage generator 44 to produce the negative voltage signal of the high voltage pulse.

In one embodiment, the positive voltage generator 40 is provided with at least two capacitors C18 and C19, and a directional control circuit 244. The switching circuit U5 of the positive voltage generator 40 has a plurality of switches X, Y and Z for switching the positive voltage generator 40 between a charging state and a discharging state. Each of the capacitors C18 and C19 are connected to the switching circuit U5 and the positive reference voltage to establish charging of the capacitors C18 and C19 in the charging state of the switching circuit U5.

Upon switch inputs "A" and "B" of switching circuit U5 receiving the low signal from the positive voltage timer 32, switches X and Y of switching circuit U5 switch to the discharging state. In the discharging state, the capacitors C18 and C19 are stacked to sum the voltage accumulated on the capacitors. That is, a positive lead of the capacitor C18 is connected to a negative lead of the capacitor C19 through the switch Y. The term "positive lead" means that there is a more positive charge on such lead as compared to the other lead. Likewise, the term "negative lead" means that there is a negative charge in reference to the other lead. Assuming that the voltage reference is +6 Volts, this would cause a +12 Volt potential to exist across the stacked capacitors C18 and C19. Further, the negative lead of the capacitor C18 is connected to the positive reference voltage (e.g., +6V), through switch X so that the positive voltage signal (e.g., +18 V) exists from the ground reference to the positive lead of the capacitor C19.

The directional control circuit 244 permits the flow of current between the positive leads of the capacitors C18 and C19 and the reference voltage in the charging state of the switching circuit U5, and prevents the flow of current between the positive leads of the capacitors C18 and C19 and the reference voltage in the discharging state of the switching circuit U5 so that the positive voltage signal is generated. The positive voltage signal is then provided to the shutter assembly 14 via line 88 through the switch Z of switching circuit U5 of the positive voltage generator 40.

As shown in FIG. 2, in one embodiment the directional control circuit 244 includes at least four diodes, as designated by the reference numeral D8 and D9. Although the directional control circuit 244 has been shown and described as the diodes D8 and D9, it should be understood that the directional control circuit 244 could be implemented in other manners. For example, the directional control circuit 244 can be implemented as any device having a P-N junction, such as a transistor, or an enhanced MOSFET.

The value of capacitors C18 and C19 can vary widely depending on the 1) output voltage, 2) load, and 3) length of time for the voltage to switch the shutter assembly 14. For example, in one embodiment the capacitors C18 and C19 can be 2.2 micro farad capacitors. The switching circuit U5 is preferably 1) an integrated circuit having a plurality of electronically controlled switches, or 2) separate electronically controlled switches.

The negative voltage generator 44 is constructed in a similar manner as the positive voltage generator 40, except as discussed hereinafter. In the charging state, the positive lead of capacitor C20 is connected to ground and the negative lead of capacitor C20 is connected to the negative reference voltage. Assuming that the negative reference voltage is −6 Volts, this would cause a −6 Volt potential to exist across the capacitor C20. In the discharging state, the positive lead of the capacitor C20 is connected to the negative reference voltage (e.g., −6 V) through the switch X so that the negative voltage signal (e.g., −12 V) exists from the ground reference to the negative lead of the capacitor C20. The negative voltage signal is output to the shutter assembly 14 via line 92 through switch Y and switch Z of switching circuit U4 of the negative voltage generator 44. The negative voltage generator 44 is also provided with a directional control circuit 250 permitting the flow of current between the negative lead of capacitor C20 and the negative reference voltage in the charging state of the switching circuit U4, and preventing the flow of current between the negative lead of the capacitor C20 and the reference voltage in the discharging state of the switching circuit U4 so that the negative voltage signal is generated.

It should be understood that the description set forth above describes a preferred embodiment of the present invention. Changes can be made without departing from the scope of the invention. For example, the capacitor C18 and/or the capacitor C19 of the positive voltage generator 40 do not have to be connected to the positive reference voltage in the charging state and/or discharging state. Any voltage, including the positive reference voltage and/or negative reference voltage, can be used so long as the capacitors C18 and C19 are charged and discharged as described herein to provide the positive voltage signal of the high voltage pulse. Further, the capacitors C18 and C19 do not have to be connected to the same voltage. Likewise, capacitor C20 of the negative voltage generator 44 does not have to be connected to the negative reference voltage in the charging and/or discharging state. Any voltage, including the positive reference voltage and/or negative reference voltage, can be used so long as capacitor C20 is charged and discharged as described herein to provide the negative voltage signal of the high voltage pulse. Furthermore, it should be understood that more capacitors and/or other energy storage devices can be used to construct the positive voltage generator 40 and/or negative voltage generator 44 of the present invention.

For example, the capacitors C18 and C19 of the positive voltage generator 40 can be connected to a first voltage to establish charging of the capacitors C18 and C19 in the charging state, and the capacitor C18 can be connected to a second voltage in the discharging state. The second voltage connected to capacitor C18 in the discharging state can be at the same or a different voltage level as the first voltage connected to capacitors C18 and C19 in the charging state. Likewise, capacitor C20 of the negative voltage generator 44 can be connected to a first voltage to charge capacitor C20 in the charging state, and connected to a second voltage in the discharging state. The second voltage connected to the capacitor C20 in the discharging state can be at the same or a different voltage level as the first voltage connected to capacitor C20 in the charging state.

When the capacitor C22 has recharged, a high signal is output to the positive voltage generator 40 via the line 96. The high signal switches the switching circuit U5 from the discharging state to the charging state to turn off the positive voltage signal. The switching circuit U4, after receiving the high signal from C16 returns to receiving a low signal and switches from the discharging state to the charging state to turn off the negative voltage signal.

Once the positive and negative voltage signals have been turned off, the stable AC waveform, as discussed above, is provided to the shutter assembly 14 through the oscillator circuit 52 and the switching circuits U3, U5, and U4 via lines 124, 254, 88 and 92. Since the switching circuits U3, U5, and U4 of the weld detect circuit 28, the positive voltage generator 40, and the negative voltage generator 44, respectively, are used to provide the stable AC waveform to the shutter assembly 14, a separate circuit is not necessary to generate the stable AC waveform or to deliver the stable AC waveform to the shutter assembly 14 after the high voltage pulse has been delivered to the shutter assembly 14. However, one of ordinary skill in the art would recognize that the control circuit 12 could be provided with a separate delivery circuit to deliver the high voltage pulse and/or the stable AC waveform to the shutter assembly 14, such as for example shown in co-pending patent application U.S. Ser. No. 10/139,837, the entire contents of which are incorporated herein by reference.

The stable AC waveform is produced as follows. The oscillating circuit 52 provides an oscillating signal to the Z1 input of the switching circuit U3 of the weld detect circuit 28 via line 124, which is then output to switch input "C" of switching circuit U5 via switch Z of switching circuit U3 and line 254. This causes switch Z of switching circuit U5 of the positive voltage generator 40 to oscillate between the Z0 and Z1 inputs. Since switching circuit U5 is at the charging state, Z0 will be the charged potential across C19, which is the positive reference voltage (e.g. +6 V), as discussed above. The Z1 input of switching circuit U5 is connected to a reference voltage of opposite polarity (e.g. −6V) through switch Y of the switching circuit U3. As such, the oscillating signal causes the switching circuit U5 of the positive voltage generator 40 to periodically switch the polarity of the signal transmitted to the shutter assembly 14 via line 88 so as to effectively deliver a square waveform (e.g. with a maximum of +6V and a minimum of −6V).

The oscillating signal input to Z1 of switching circuit U3 is also output via switch Z of switching circuit U3 to the switch input "B" of switching circuit U4 of the negative voltage generator 44, thereby causing switch Y of switching circuit U4 to oscillate between Y0 and Y1. Switch Y of switching circuit U4 is connected to Z1 of switching circuit U4 so that when switch input "C" of switching circuit U4 is high, the switch Z of switching circuit U4 oscillates between Y0 and Y1. Since switching circuit U4 is at the charging state, Y0 will be the charged potential across C20, which is the negative reference voltage (e.g. −6V), as discussed above. Y1 is connected to a reference voltage of opposite polarity (e.g. +6V) and, as such, the oscillating signal causes the switching circuit U4 of the negative voltage generator 44 to periodically switch the polarity of the signal transmitted to the signal transmitted to the shutter assembly 14 via line 92 so as to effectively deliver a square waveform (e.g. with a maximum of +6V and a minimum of −6V) which is inversely synchronized with the square waveform provided by the positive voltage generator 40 via line 88.

Since the square waveforms produced by switching circuits U5 and U4 are inversely synchronized, the AC waveform received by the shutter assembly 14, which is not referenced to ground, is effectively a square waveform which has a maximum equal to the difference between the maximum of the square waveform output by the positive voltage generator 40 and the minimum of the square waveform output by the negative voltage generator 44 (e.g., max=+6V−(−6V)=+12V), and a minimum equal to the difference between the minimum of the square waveform output by the positive voltage generator 40 and the maximum of the square waveform output by the negative voltage generator 44 (e.g., min=−6V−6V=−12V).

When the sensor circuit 24 no longer senses the welding arc, the signal on line 112 switches to a "low" state, thereby turning off the transistor Q8. This permits the capacitor C21 to discharge through the resistor R28 causing a low state signal to be delivered on the line 116 after a predetermined time period. The low state signal is received by the switch input "C" of the switching circuit U4 and by the switch input "C" of the switching circuit U3 which thereby causes a "low" state signal to be output to the switch input "C" of switching circuit U5 via switch Z of the switching circuit U3. As a result, switching circuit U5 and U4 output the same reference voltage (e.g. +6V), thereby causing the shutter assembly 14 to switch from the dark state to the light state.

Referring now to FIG. 3, shown in schematic diagram form is another implementation of a weld detect circuit (labeled therein as 28*a*), a positive voltage generator (labeled therein as 40*a*), and a negative voltage generator (labeled therein as 44*a*). The weld detect circuit 28*a*, the positive voltage generator 40*a*, and the negative voltage generator 44*a* depicted in FIG. 3 are similar in construction and function to the weld detect circuit 28, the positive voltage generator 40, and the negative voltage generator 44, respectively, as discussed above with reference to FIG. 2, except that the weld detect circuit 28*a*, the positive voltage generator 40*a*, and the negative voltage generator 44*a* are constructed so as to reduce the "bleeding-off" of charge from the capacitors by the diodes, and to reduce fluctuations in the dark state drive signal caused by voltage drops across the diodes. Therefore, for purposes of brevity, similar components of the weld detect circuit 28*a*, the positive voltage generator 40*a*, and the negative voltage generator 44*a* are labeled in FIG. 3 with the same number prefix, but with an additional alphanumeric suffix "a", as the components of the weld detect circuit 28, the positive voltage generator 40, and the negative voltage generator 44 depicted in FIG. 2. Further, for purposes of brevity, only the differences in operation of the weld detect circuit 28*a*, the positive voltage generator 40*a*, and the negative voltage generator 44*a* are discussed in further detail below.

The output of the positive voltage timer 32 at capacitor C22 is connected to switch inputs "A" and "C" of a switching circuit U5*a* of the positive voltage generator 40*a* to cause the positive voltage generator 40*a* to produce the positive voltage of the high voltage pulse. The output of the negative voltage timer 36 at capacitor C16 is connected to switch inputs "A" and "C" of a switching circuit U4*a* of the negative voltage generator 44*a* to cause the negative voltage generator 44*a* to produce the negative voltage signal of the high voltage pulse.

The positive voltage generator 40*a* is provided with one capacitor C19*a* and a directional control circuit 244*a*. The capacitor C19*a* of the positive voltage generator 40*a* functions similarly to the capacitors C18 and C19 of the positive voltage generator 40 discussed with reference to FIG. 2. The capacitor C19*a* of the positive voltage generator 40*a* has a high capacitance, e.g. 4.7 micro farads. During the charging state, the capacitor C19*a* is charged with reference to the positive reference voltage and the negative reference voltage via switch X of switching circuit U5*a* so as to effectively connect capacitor C19*a* to a voltage having a magnitude of the difference between the positive reference voltage and the negative reference voltage across the capacitor C19*a*. Assuming that the positive reference voltage is +6 Volts and the negative reference voltage is −6 Volts, this would cause a potential with a magnitude of 12 Volts to exist across the capacitor C19*a* in the charging state of switching circuit U5*a*.

In the discharging state, upon switch inputs "A" and "C" of switching circuit U5*a* receiving the low signal from the positive voltage timer 32, switches X and Z of switching circuit U5*a* switch so that a positive lead of the capacitor C19*a* is connected to line 88 via switch Z, and a negative lead of the capacitor C19*a* is connected to the positive reference voltage (e.g., +6V) via switch X. As a result, the positive voltage signal (e.g., +18V) exists from the ground reference to the positive lead of the capacitor C19*a*. Additionally, to reduce noise, the positive voltage generator 40*a* can further include a capacitor C24 connected between the positive lead of the capacitor C19*a* and ground, such as shown for example in FIG. 3.

The directional control circuit 244*a*, in one embodiment, includes at least two diodes, as designated in FIG. 3 by the reference numeral D8*a*. The directional control circuit 244*a* permits the flow of current between the positive lead of the capacitor C19*a* and the reference voltage in the charging state of the switching circuit U5, and prevents the flow of current between the positive lead of the capacitor C19*a* in the discharging state of the switching circuit U5 so that the positive voltage signal is generated. The positive voltage signal is provided to the shutter assembly 14 via line 88 through switch Z of switching circuit U5a of the positive voltage generator 40a.

In the negative voltage generator 44a, in the charging state, a positive lead of a capacitor C20a is connected to ground and a negative lead of capacitor C20a is connected to a negative reference voltage. Assuming that the negative reference voltage is −6 Volts, this would cause a −6 Volt potential to exist across the capacitor C20a. In the discharging state, the positive lead of the capacitor C20a is connected to the negative reference voltage (e.g., −6V) through the switch X of switching circuit U4a so that the negative voltage signal (e.g., −12V) exists from the ground reference to the negative lead of the capacitor C20a. Additionally, to reduce noise, the negative voltage generator 44a can further include a capacitor C25 connected between the negative lead of capacitor C20a and ground, such as shown for example in FIG. 3.

The negative voltage generator 44a is also provided with a directional control circuit 250a, which in one embodiment includes one diode, as designated in FIG. 3 by the reference numeral D5a. The directional control circuit 250a permits the flow of current between the negative lead of the capacitor C20a and the negative reference voltage in the charging state of the switching circuit U4a, and prevents the flow of current between the negative lead of the capacitor C20a and the reference voltage in the discharging state of the switching circuit U4a so that the negative voltage signal is generated. The negative voltage signal is outputted to the shutter assembly 14 via line 92 through switch Z of switching circuit U4a of the negative voltage generator 44a.

It should be understood that the description set forth above describes a preferred embodiment of the present invention. Changes can be made without departing from the scope of the invention. For example, the capacitor C19a of the positive voltage generator 40a does not have to be connected to the positive reference voltage and/or the negative reference voltage in the charging state and/or discharging state. Any voltages, including the positive reference voltage and/or negative reference voltage, can be used so long as the capacitor C19a is charged and discharged as described herein to provide the positive voltage signal of the high voltage pulse. Likewise, capacitor C20a of the negative voltage generator 44a does not have to be connected to the negative reference voltage in the charging and/or discharging state. Any voltage, including the positive reference voltage and/or negative reference voltage, can be used so long as capacitor C20a is charged and discharged as described herein to provide the negative voltage signal of the high voltage pulse. Furthermore, it should be understood that more capacitors and/or other energy storage devices can be used to construct the positive voltage generator 40a and/or negative voltage generator 44a of the present invention For example, the capacitor C19a of the positive voltage generator 40a can be connected to a first voltage to establish charging of the capacitor C19a in the charging state, and the capacitor C19a can be connected to a second voltage in the discharging state. The second voltage level connected to capacitor C19a in the discharging state can be at the same or a different voltage level as the first voltage connected to capacitor C19a in the charging state. Likewise, capacitor C20a of the negative voltage generator 44a can be connected to a first voltage to charge capacitor C20a in the charging state and connected to a second voltage in the discharging state. The second voltage connected to capacitor C20a in the discharging state can be at the same or a different voltage level as the first voltage connected to the capacitor C20a in the charging state.

When the capacitor C22 of the positive voltage timer 32 has recharged, a high signal is outputted to the positive voltage generator 40a via the line 96. The high signal switches the switching circuit U5a from the discharging state to the charging state to turn off the positive voltage signal. The switching circuit U4 of the negative voltage generator 44a, after receiving the high signal from capacitor C16 of the negative voltage timer 36, returns to receiving a low signal and switches from the discharging state to the charging state to turn off the negative voltage signal.

Once the positive and negative voltage signals have been turned off, the stable AC waveform is provided to the shutter assembly 14 through the oscillator circuit 52 and the switching circuits U3a, U5a, and U4a via lines 124, 254, 88 and 92. The stable AC waveform is produced as follows.

The oscillating circuit 52a provides an oscillating signal to switch input "B" of the switching circuit U3a of the weld detect circuit 28a via line 124. This causes switch Y of switching circuit U3a of the weld detect circuit 28a to oscillate between Y0 and Y1 inputs. Y1 is connected to the negative reference voltage (e.g. −6V) and Y0 is connected to a reference voltage of opposite polarity (e.g. +6V) via switch Y of switching circuit U5a.

The output of switch Y of switching circuit U3a is connected to the Z1 input of switching circuit U5a. When switch input "C" of switching circuit U5a is high, the output of switch Z of switching circuit U5a oscillates between Y0 and Y1, i.e. the output of switch Z of switching circuit U5a of the positive voltage generator 40a will transmit a signal which periodically switches in polarity to the shutter assembly 14 via line 88 so as to effectively deliver a square waveform (e.g. with a maximum of +6V and a minimum of −6V).

The oscillating signal is also output via line 124 to the switch input "B" of switching circuit U4a of the negative voltage generator 44a, thereby causing the output of switch Y of switching circuit U4a to oscillate between Y0 and Y1. The output of switch Y of switching circuit U4a is connected to Z0 of switching circuit U4a so that when switch input "C" of switching circuit U4a is low, the output of switch Z of switching circuit U4a oscillates between Y0 and Y1. Y0 is connected to the negative reference voltage (e.g. −6V) and Y1 is connected to a reference voltage of opposite polarity (e.g. +6V) via switch Y of switching circuit U5a. As such, the output of switch Z of switching circuit U4a of the negative voltage generator 40a will transmit a signal which periodically switches in polarity to the shutter assembly 14 via line 92 so as to effectively deliver a square waveform (e.g. with a maximum of +6V and a minimum of −6V) which is inversely synchronized with the square waveform provided by the positive voltage generator 40a via line 88.

Since the square waveforms outputted by switching circuits U5a and U4a are inversely synchronized, the AC waveform received by the shutter assembly 14, which is not referenced to ground, is effectively a square waveform which has a maximum equal to the difference between the maximum of the square waveform output by the positive voltage generator 40a and the minimum of the square waveform output by the negative voltage generator 44a (e.g., max=+6V−(−6V)=+12V), and a minimum equal to the difference between the minimum of the square waveform output by the positive voltage generator 40a and the maximum of the square waveform output by the negative voltage generator 44a (e.g., min=−6V−6V=−12V).

When the sensor circuit 24 no longer senses the welding arc, the signal on line 112 switches to a "low" state, thereby turning off the transistor Q8 and causing the capacitor C21 to discharge through the resistor R28 and switch line 116 to a low state after a predetermined time period. The low state signal on line 116 is received by the switch input "B" of the switching circuit U5a, which thereby causes switch Y of switching circuit U5a to output the signal on the Y0 input, which is connected to the negative reference voltage (e.g. −6V) via switch Z of switching circuit U3a. The negative reference voltage is outputted from switch Y of switching circuit U5a to line 88 via switch Y of switching circuit U3a and switch Z of switching circuit U5a. The negative reference voltage is also outputted from switch Y of switching circuit U5a to line 92 via switch Y and switch Z of switching circuit U4a. As a result, switching circuit U5a of the positive voltage generator 40a and switching circuit U4a of the negative voltage generator 44a output the same voltage (e.g. −6V), thereby causing the shutter assembly 14 to switch from the dark state to the light state.

Figure 5:
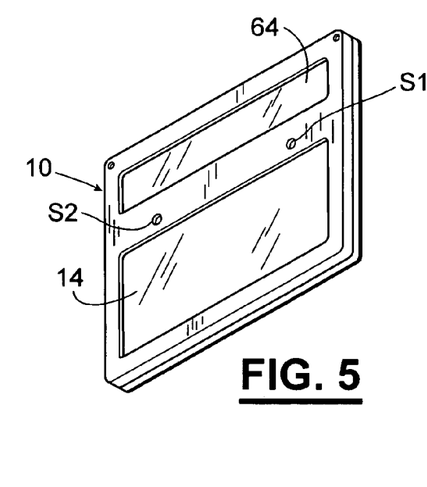
FIG. 5 is a front perspective view of the eye protection device.

Referring now to FIG. 5, shown therein is a front perspective view of the eye protection device 10. The sensor circuit 24 of the eye protection device 10 includes a pair of spatially disposed light detectors, such as phototransistors S1 and S2, for sensing the welding arc.

The eye protection device 10 can be provided with a plurality of controls for controlling various settings thereof. For example, the eye protection device 10 can be provided with a knob (not shown) or other control mechanism, such as one or more buttons, connected to any suitable component for adjusting the settings, e.g., sensitivity, delay, or shade, of the eye protection device 10.

Figure 6:
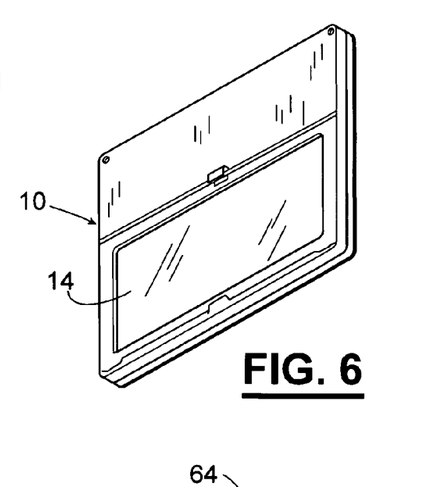
FIG. 6 is a rear perspective view of the eye protection device.
Figure 7:
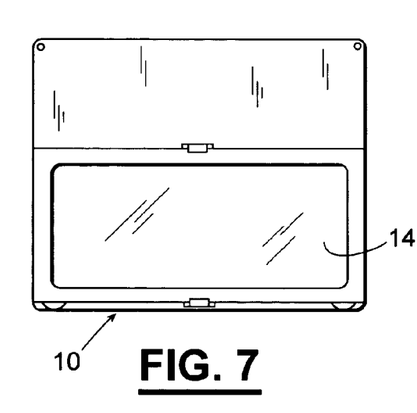
FIG. 7 is a rear elevational view of the eye protection device.
Figure 8:
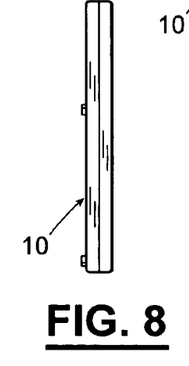
FIG. 8 is a side elevational view of the eye protection device.
Figure 9:
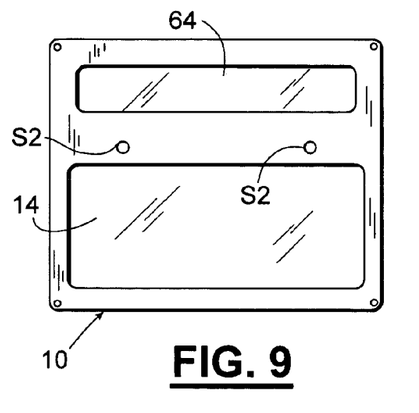
FIG. 9 is a front elevational view of the eye protection device.

FIG. 6 is a rear perspective view of the eye protection device 10. FIG. 7 is a front elevational view of the eye protection device 10. FIG. 8 is a side elevational view of the eye protection device 10. FIG. 9 is a front elevational view of the eye protection device 10.

One skilled in the art will recognize that the present invention is susceptible to numerous modifications and variations. For example, the shutter assembly 14 and the control circuit 12 can be implemented in a cassette connectable to a welding helmet, or integrated into the welding helmet. Further, the user controls can be on the cassette or separate from the cassette. For example, the user controls can be implemented as a "pig-tail."

The embodiments of the invention discussed herein are intended to be illustrative and not limiting. Other embodiments of the invention will be obvious to those skilled in the art in view of the above disclosure. Changes may be made in the embodiments of the invention described herein, or in the parts or the elements of the embodiments described herein, or in the steps or sequence of steps of the methods described herein, without departing from the spirit and/or the scope of the invention.

What is claimed is:

1. An auto darkening eye protection device comprising:
 a shutter assembly adjustable between a light state and a dark state; and
 a control circuit comprising:
  a power supply having a voltage;
  a sensing circuit sensing an occurrence of a welding arc and providing an output indicative of the occurrence of the welding arc;
  a weld detect circuit receiving the output of the sensing circuit, the weld detect circuit enabling a dark state drive signal to be delivered to the shutter assembly; and
  a positive voltage generator and a negative voltage generator receiving power from the power supply and cooperating to output the dark state drive signal to the shutter assembly to switch the shutter assembly from the light state to the dark state upon enablement by the weld detect circuit, the dark state drive signal including a high voltage pulse followed by a stable AC waveform, the high voltage pulse being formed by a positive voltage signal and a negative voltage signal, the positive voltage signal having a magnitude greater than the voltage of the power supply.

2. The auto darkening eye protection device of claim 1, wherein the positive voltage generator and the negative generator are coupled to the shutter assembly such that the output of the positive voltage generator and the negative generator passes to the shutter assembly without passing through a high voltage driver.

3. The auto darkening eye protection device of claim 1, wherein the positive voltage signal and the negative voltage signal are each referenced to ground.

4. The auto darkening eye protection device of claim 1, wherein the high voltage pulse has a voltage in a range from about 15 Volts to about 120 Volts, and a time period from about 10 microseconds to about 100 milliseconds.

5. The auto darkening eye protection device of claim 1, wherein the leading edges of the positive and negative voltage signals are synchronized.

6. The auto darkening eye protection device of claim 1, wherein the positive voltage generator includes:
 a switching circuit having a charging state and a discharging state;
 at least two capacitors, each of the capacitors connected to the switching circuit and a first voltage to establish charging of the capacitors in the charging state of the switching circuit, and a negative lead of one of the capacitors electrically connected to a positive lead of another one of the capacitors and a negative lead of another one of the capacitors electrically connected to a second voltage in the discharging state of the switching circuit; and
 a directional control circuit connected to the capacitors to permit the flow of current between the positive leads of the capacitors and the first voltage in the charging state of the switching circuit, and to prevent the flow of current between the positive leads of the capacitors and the first voltage in the discharging state of the switching circuit.

7. The auto darkening eye protection device of claim 6, wherein the directional control circuit of the positive voltage generator includes at least four diodes.

8. The auto darkening eye protection device of claim 6, wherein the switching circuit of the positive voltage generator operates at voltage levels with a magnitude of no greater than 20 Volts.

9. The auto darkening eye protection device of claim 1, wherein the positive voltage generator includes:
 a switching circuit having a charging state and a discharging state;
 at least one capacitor connected to the switching circuit and a first voltage to establish charging of the capacitor in the charging state of the switching circuit, and a negative lead of the capacitor electrically connected to a second voltage in the discharging state of the switching circuit; and
 a directional control circuit connected to the capacitor to permit the flow of current between the positive lead of the capacitor and the first voltage in the charging state of the switching circuit, and to prevent the flow of current between the positive lead of the capacitor and the first voltage in the discharging state of the switching circuit.

10. The auto darkening eye protection device of claim 9, wherein the directional control circuit of the positive voltage generator includes at least two diodes.

11. The auto darkening eye protection device of claim 9, wherein the switching circuit of the positive voltage generator operates at voltage levels with a magnitude of no greater than 20 Volts.

12. The auto darkening eye protection device of claim 1, wherein the negative voltage generator includes:
  a switching circuit having a charging state and a discharging state;
  at least one capacitor, the capacitor connected to the switching circuit and a first voltage to establish charging of the capacitor in the charging state of the switching circuit, and a positive lead of the capacitor electrically connected to a second voltage in the discharging state of the switching circuit; and
  a directional control circuit connected to the capacitor to permit the flow of current between the negative lead of the capacitor and the first voltage in the charging state of the switching circuit, and to prevent the flow of current between the negative lead of the capacitor and the first voltage in the discharging state of the switching circuit.

13. The auto darkening eye protection device of claim 12, wherein the directional control circuit of the negative voltage generator includes at least one diode.

14. The auto darkening eye protection device of claim 13, wherein the switching circuit of the negative voltage generator operates at voltage levels with a magnitude of no greater than 20 Volts.

15. An auto darkening eye protection device comprising:
  a shutter assembly adjustable between a light state and a dark state; and
  a control circuit comprising:
    a sensing circuit sensing an occurrence of a welding arc and providing an output indicative of the occurrence of the welding arc;
    a weld detect circuit receiving the output of the sensing circuit, the weld detect circuit enabling a dark state drive signal to be delivered to the shutter assembly;
    a power supply supplying power to the control circuit, the power supply comprising a reference generator generating at least two reference voltages;
    a positive voltage generator and a negative voltage generator receiving power from the power supply and cooperating to output the dark state drive signal to the shutter assembly to switch the shutter assembly from the light state to the dark state upon enablement by the weld detect circuit, the dark state drive signal including a high voltage pulse, the high voltage pulse being formed by a positive voltage signal and a negative voltage signal, the positive voltage signal being generated by the positive voltage generator with one of the reference voltages and the negative voltage signal being generated by the negative voltage generator with the other reference voltage; and
    wherein the positive voltage generator and the negative generator are coupled to the shutter assembly such that the output of the positive voltage generator and the negative generator passes to the shutter assembly without passing through a high voltage driver.

16. The auto darkening eye protection device of claim 15, wherein the reference generator produces a positive reference voltage and a negative reference voltage.

17. The auto darkening eye protection device of claim 16, wherein the reference generator provides the positive reference voltage to the positive voltage generator.

18. The auto darkening eye protection device of claim 16, wherein the reference generator provides the negative reference voltage to the negative voltage generator.

19. An auto darkening eye protection device comprising:
  a shutter assembly adjustable between a light state and a dark state; and
  a control circuit comprising:
    a sensing circuit sensing an occurrence of a welding arc and providing an output indicative of the occurrence of the welding arc;
    a weld detect circuit receiving the output of the sensing circuit, the weld detect circuit enabling a dark state drive signal to be delivered to the shutter assembly;
    a power supply supplying power to the control circuit, the power supply comprising a reference generator generating at least two reference voltages;
    a positive voltage generator and a negative voltage generator receiving power from the power supply and cooperating to output the dark state drive signal to the shutter assembly to switch the shutter assembly from the light state to the dark state upon enablement by the weld detect circuit, the dark state drive signal including a high voltage pulse, the high voltage pulse being formed by a positive voltage signal and a negative voltage signal, the positive voltage signal being generated by the positive voltage generator with one of the reference voltages and the negative voltage signal being generated by the negative voltage generator with the other reference voltage; and
    wherein the power supply is further provided with a battery power supply and a solar power supply, and wherein additional current is provided to the battery power supply by the solar power supply when the control circuit is in the dark state.

20. An auto darkening eye protection device comprising:
  a shutter assembly adjustable between a light state and a dark state; and
  a control circuit comprising:
    a sensing circuit sensing an occurrence of a welding arc and providing an output indicative of the occurrence of the welding arc;
    a weld detect circuit receiving the output of the sensing circuit, the weld detect circuit enabling a dark state drive signal to be delivered to the shutter assembly;
    a power supply supplying power to the control circuit, the power supply comprising a reference generator generating at least two reference voltages; and
    a positive voltage generator and a negative voltage generator receiving power from the power supply and cooperating to output the dark state drive signal to the shutter assembly to switch the shutter assembly from the light state to the dark state upon enablement by the weld detect circuit, the dark state drive signal including a high voltage pulse, the high voltage pulse being formed by a positive voltage signal and a negative voltage signal, the positive voltage signal being generated by the positive voltage generator with one of the reference voltages and the negative voltage signal being generated by the negative voltage generator with the other reference voltage; and wherein the power supply is further provided with a battery power supply and a solar power supply, and the control circuit further comprises a power conservation circuit, the power conservation circuit causing the reference generator of the control circuit to only utilize or supply power from the battery power supply when the solar power supply supplies power to the power conservation circuit.

21. The auto darkening eye protection device of claim 20, wherein the reference generator is a charge pump and the oscillator circuit is used to supply an AC signal to the charge pump.

22. An auto darkening eye protection device comprising:
a shutter assembly adjustable between a light state and a dark state; and
a control circuit comprising:
a sensing circuit sensing an occurrence of a welding arc and providing an output indicative of the occurrence of the welding arc;
a weld detect circuit receiving the output of the sensing circuit, the weld detect circuit enabling a dark state drive signal to be delivered to the shutter assembly; and
a positive voltage generator and a negative voltage generator receiving power from the power supply and cooperating to output the dark state drive signal to the shutter assembly to switch the shutter assembly from the light state to the dark state upon enablement by the weld detect circuit, the dark state drive signal including a high voltage pulse followed by a stable AC waveform, the high voltage pulse being formed by a positive voltage signal and a negative voltage signal, the positive voltage signal being generated for a predetermined period of time.

23. The auto darkening eye protection device of claim 22, wherein the positive voltage generator and the negative generator are coupled to the shutter assembly such that the output of the positive voltage generator and the negative generator passes to the shutter assembly without passing through a high voltage driver.

24. The auto darkening eye protection device of claim 22, wherein the positive voltage signal and the negative voltage signal are each referenced to ground.

25. The auto darkening eye protection device of claim 22, wherein the high voltage pulse has a voltage in a range from about 15 Volts to about 120 Volts, and a time period from about 10 microseconds to about 100 milliseconds.

26. The auto darkening eye protection device of claim 22, wherein the leading edges of the positive and negative voltage signals are synchronized.

27. The auto darkening eye protection device of claim 22, wherein the positive voltage generator includes:
a switching circuit having a charging state and a discharging state;
at least two capacitors, each of the capacitors connected to the switching circuit and a first voltage to establish charging of the capacitors in the charging state of the switching circuit, and a negative lead of one of the capacitors electrically connected to a positive lead of another one of the capacitors and a negative lead of another one of the capacitors electrically connected to a second voltage in the discharging state of the switching circuit; and
a directional control circuit connected to the capacitors to permit the flow of current between the positive leads of the capacitors and the first voltage in the charging state of the switching circuit, and to prevent the flow of current between the positive leads of the capacitors and the first voltage in the discharging state of the switching circuit.

28. The auto darkening eye protection device of claim 27, wherein the directional control circuit of the positive voltage generator includes at least four diodes.

29. The auto darkening eye protection device of claim 27, wherein the switching circuit of the positive voltage generator operates at voltage levels with a magnitude of no greater than 20 Volts.

30. The auto darkening eye protection device of claim 22, wherein the positive voltage generator includes:
a switching circuit having a charging state and a discharging state;
at least one capacitor connected to the switching circuit and a first voltage to establish charging of the capacitor in the charging state of the switching circuit, and a negative lead of the capacitor electrically connected to a second voltage in the discharging state of the switching circuit; and
a directional control circuit connected to the capacitor to permit the flow of current between the positive lead of the capacitor and the first voltage in the charging state of the switching circuit, and to prevent the flow of current between the positive lead of the capacitor and the first voltage in the discharging state of the switching circuit.

31. The auto darkening eye protection device of claim 30, wherein the directional control circuit of the positive voltage generator includes at least two diodes.

32. The auto darkening eye protection device of claim 30, wherein the switching circuit of the positive voltage generator operates at voltage levels with a magnitude of no greater than 20 Volts.

33. The auto darkening eye protection device of claim 22, wherein the negative voltage generator includes:
a switching circuit having a charging state and a discharging state;
at least one capacitor, the capacitor connected to the switching circuit and a first voltage to establish charging of the capacitor in the charging state of the switching circuit, and a positive lead of the capacitor electrically connected to a second voltage in the discharging state of the switching circuit;
a directional control circuit connected to the capacitor to permit the flow of current between the negative lead of the capacitor and the first voltage in the charging state of the switching circuit, and to prevent the flow of current between the negative lead of the capacitor and the first voltage in the discharging state of the switching circuit.

34. The auto darkening eye protection device of claim 33, wherein the directional control circuit of the negative voltage generator includes at least one diode.

35. The auto darkening eye protection device of claim 33, wherein the switching circuit of the negative voltage generator operates at voltage levels with a magnitude of no greater than 20 Volts.

* * * * *

UNITED STATES PATENT AND TRADEMARK OFFICE
CERTIFICATE OF CORRECTION

PATENT NO. : 7,026,593 B2 Page 1 of 1
APPLICATION NO. : 10/915929
DATED : April 11, 2006
INVENTOR(S) : Thomas J. Hamilton It is certified that error appears in the above-identified patent and that said Letters Patent is hereby corrected as shown below:

Column 6, Line 18: After the word "manufactured" insert the word --by--.

Signed and Sealed this

Tenth Day of April, 2007

JON W. DUDAS
*Director of the United States Patent and Trademark Office*